(12) United States Patent
Hedman (10) Patent No.: US 8,272,143 B1
(45) Date of Patent: Sep. 25, 2012

(54) SYSTEM AND PROCESS FOR REMOVING OR TREATING HARMFUL BIOLOGICAL AND ORGANIC SUBSTANCES WITHIN STRUCTURES AND ENCLOSURES

(76) Inventor: David Hedman, Ojai, CA (US)

(*) Notice: Subject to any disclaimer, the term of this patent is extended or adjusted under 35 U.S.C. 154(b) by 2705 days.

(21) Appl. No.: 10/644,553

(22) Filed: Aug. 19, 2003

Related U.S. Application Data (63) Continuation-in-part of application No. 10/371,826, filed on Feb. 20, 2003, now Pat. No. 8,221,678, which is a continuation-in-part of application No. 10/313,901, filed on Dec. 5, 2002, now abandoned.

(60) Provisional application No. 60/358,222, filed on Feb. 20, 2002, provisional application No. 60/358,223, filed on Feb. 20, 2002.

(51) Int. Cl.
  *A61L 9/00* (2006.01)
  *A62B 7/08* (2006.01)
  *A01M 1/20* (2006.01)
  *F26B 19/00* (2006.01)
  *B60H 3/00* (2006.01)
  *B60H 1/02* (2006.01)

(52) U.S. Cl. ........... 34/201; 422/1; 422/3; 422/4; 422/5; 422/28; 422/119; 422/125; 422/292; 422/305; 43/124; 43/144; 34/100; 34/380; 454/156; 454/159; 454/160

(58) Field of Classification Search ............... 422/1, 3–5, 422/28, 119, 125, 292, 305; 43/124, 144; 34/380, 100, 201; 454/156, 159, 160
See application file for complete search history.

(56) References Cited

U.S. PATENT DOCUMENTS

| | | | |
|---|---|---|---|
| 919,827 A | | 4/1909 | Cochrane |
| 923,368 A | | 6/1909 | Myser |
| 1,885,854 A | | 11/1932 | Montellano |
| 1,943,613 A | | 1/1934 | Lewis |
| 1,948,228 A | | 2/1934 | Urban |
| 2,040,110 A | | 5/1936 | Tahvonen et al. |
| 2,114,494 A | | 4/1938 | Hummel et al. |
| 2,171,315 A | * | 8/1939 | Rennerfelt .................. 422/1 |

(Continued)

FOREIGN PATENT DOCUMENTS

CA     2205673     11/1998

(Continued)

OTHER PUBLICATIONS

Internet Printout of "Preventing IAQ Problems at their source: Maintenance and Housekeeping", (Jan. 9, 2002).*

(Continued)

*Primary Examiner* — Jill Warden
*Assistant Examiner* — Monzer Chorbaji
(74) *Attorney, Agent, or Firm* — Kelly & Kelley, LLP (57) ABSTRACT

A process for removing or treating harmful biological and organic substances within an enclosure includes heating the ambient air within the enclosed area to a predetermined temperature over time to cause harmful biological or organic substances to be destroyed or migrate into the ambient air. Temperature and pressure levels are monitored through the treatment process. Contaminated objects or areas may be subjected to biocides, irradiation, or even freezing as part of the treatment process. The air removed from the enclosure is preferably passed through an incinerator, a filter or an irradiation device and the heated air is re-circulated to enhance efficiency.

43 Claims, 6 Drawing Sheets

U.S. PATENT DOCUMENTS

| | | | |
|---|---|---|---|
| 2,318,820 A | 5/1943 | Voigt et al. | |
| 2,386,676 A | 10/1945 | French | |
| 2,606,440 A | 8/1952 | Willey | |
| 3,041,684 A * | 7/1962 | Dawson et al. | 422/292 |
| 3,107,974 A * | 10/1963 | Potapenko | 422/4 |
| 3,265,862 A | 8/1966 | Smith, Jr. et al. | |
| 3,420,439 A | 1/1969 | Meckler | |
| 3,505,989 A * | 4/1970 | Truhan | 600/21 |
| 3,748,803 A | 7/1973 | Widerby et al. | |
| 3,750,327 A | 8/1973 | Thybault | |
| 3,831,332 A | 8/1974 | Weese | |
| 3,846,072 A | 11/1974 | Patterson | |
| 3,964,268 A | 6/1976 | DiPeri | |
| 3,966,407 A | 6/1976 | Zuckerberg et al. | |
| 4,045,880 A | 9/1977 | Steffen | |
| 4,205,381 A | 5/1980 | Games et al. | |
| 4,277,926 A | 7/1981 | Sherman et al. | |
| 4,597,192 A | 7/1986 | Sfondrini et al. | |
| 4,625,432 A | 12/1986 | Baltes | |
| 4,676,152 A | 6/1987 | Tsuji et al. | |
| 4,682,424 A | 7/1987 | Irving | |
| 4,817,329 A | 4/1989 | Forbes | |
| 4,823,520 A | 4/1989 | Ebeling et al. | |
| 4,864,942 A | 9/1989 | Fochtman et al. | |
| 4,902,315 A | 2/1990 | Spicer | |
| 4,918,857 A | 4/1990 | Wade et al. | |
| 4,953,320 A | 9/1990 | Nelson | |
| 4,955,146 A | 9/1990 | Bollinger | |
| 4,958,456 A * | 9/1990 | Chaudoin et al. | 43/124 |
| 4,961,283 A | 10/1990 | Forbes | |
| 4,989,363 A | 2/1991 | Doernemann | |
| 5,022,165 A | 6/1991 | Beswick | |
| 5,030,423 A | 7/1991 | Obee et al. | |
| 5,058,313 A | 10/1991 | Tallon | |
| 5,069,618 A | 12/1991 | Nieberding | |
| 5,090,972 A * | 2/1992 | Eller et al. | 95/10 |
| 5,096,474 A | 3/1992 | Miller, Jr. et al. | |
| 5,109,916 A | 5/1992 | Thompson | |
| 5,120,512 A | 6/1992 | Masuda | |
| 5,152,077 A | 10/1992 | Liang | |
| 5,155,924 A | 10/1992 | Smith | |
| 5,192,343 A | 3/1993 | Henry | |
| 5,203,108 A | 4/1993 | Washburn, Jr. | |
| 5,219,226 A | 6/1993 | James | |
| 5,221,520 A | 6/1993 | Cornwell | |
| 5,225,167 A | 7/1993 | Wetzel | |
| 5,226,244 A * | 7/1993 | Carter et al. | 34/191 |
| 5,244,480 A | 9/1993 | Henry | |
| 5,293,700 A | 3/1994 | Ishii | |
| 5,348,704 A | 9/1994 | Tanaka | |
| 5,349,778 A | 9/1994 | Chu | |
| 5,369,892 A | 12/1994 | Dhaemers | |
| 5,378,086 A | 1/1995 | Campbell, Jr. et al. | |
| 5,387,403 A | 2/1995 | Ikeuchi et al. | |
| 5,416,727 A | 5/1995 | Shook et al. | |
| 5,442,876 A | 8/1995 | Pedersen | |
| 5,491,092 A | 2/1996 | Colvin | |
| 5,556,607 A | 9/1996 | Childers et al. | |
| 5,590,478 A | 1/1997 | Furness | |
| 5,590,830 A | 1/1997 | Kettler et al. | |
| 5,612,001 A | 3/1997 | Matschke | |
| 5,618,333 A * | 4/1997 | Buchholz et al. | 95/214 |
| 5,656,063 A | 8/1997 | Hsu | |
| 5,728,185 A | 3/1998 | Buchholz, Jr. et al. | |
| 5,761,908 A | 6/1998 | Oas et al. | |
| 5,768,907 A | 6/1998 | Lee | |
| 5,806,238 A | 9/1998 | Brenner et al. | |
| 5,837,040 A | 11/1998 | Caughron et al. | |
| 5,874,050 A | 2/1999 | Matias | |
| 5,960,556 A | 10/1999 | Jansen | |
| 5,960,558 A | 10/1999 | Bourgault | |
| 5,979,472 A | 11/1999 | Lowery et al. | |
| 6,032,474 A | 3/2000 | Dale et al. | |
| 6,141,901 A | 11/2000 | Johnson et al. | |
| 6,162,393 A | 12/2000 | De Bruiju et al. | |
| 6,199,770 B1 | 3/2001 | King et al. | |
| 6,279,261 B1 * | 8/2001 | Binker et al. | 43/125 |
| 6,289,974 B1 | 9/2001 | De Gregoria | |
| 6,327,812 B1 | 12/2001 | Hedman et al. | |
| 6,383,449 B1 | 5/2002 | Pennekamp et al. | |
| 6,451,152 B1 | 9/2002 | Holmes et al. | |
| 6,494,934 B2 | 12/2002 | Fukushima | |
| 6,588,140 B1 | 7/2003 | Johnson et al. | |
| 6,612,067 B2 | 9/2003 | Topp | |
| 6,656,424 B1 | 12/2003 | Deal | |
| 6,878,177 B2 | 4/2005 | Lohr et al. | |
| 6,892,491 B2 | 5/2005 | Hedman | |
| 6,911,177 B2 * | 6/2005 | Deal | 422/24 |
| 6,962,619 B1 | 11/2005 | DeRosa et al. | |
| 7,690,148 B2 | 4/2010 | Hedman | |
| 2003/0100465 A1 | 5/2003 | Kilkenny et al. | |
| 2003/0230477 A1 | 12/2003 | Fink et al. | |
| 2004/0028554 A1 | 2/2004 | Hedman | |

FOREIGN PATENT DOCUMENTS

| | | |
|---|---|---|
| DE | 33 38 848 A1 | 5/1985 |
| DE | 3421719 A1 | 12/1985 |
| DE | 40 25 828 A1 | 2/1992 |
| DE | 42 05 459 A1 | 8/1993 |
| DE | 43 08 585 A1 | 9/1994 |
| EP | 676138 A1 | 10/1995 |
| EP | 0 676 138 A1 | 8/1997 |
| JP | 2187115 A | 7/1990 |
| JP | 2000116757 A | 4/2000 |
| WO | 9730802 A1 | 8/1997 |
| WO | 01/91858 A1 | 12/2001 |

OTHER PUBLICATIONS

"Volatile Organic Compounds and Building Bake-Out" from the California Indoor Air Quality Program et al. Occupational Medicine: State of the Art Reviews—vol. 4, No. 4, Oct.-Dec. 1989, pp. 695-711.

"First Results of a Pilot Decontamination in a PCP Polluted Building by Means of a Humidity Controlled Thermal Process"—Abridged translation. By W. Von Rotberg et al.

George A. Dean, "Heat as a Means of Controlling Mill Insects", Journal, 1911, pp. 142-161, vol. 4, Journal of Economic Entomology Publishing Co., USA.

W.C. O'Kane and W.A. Osgood, "Studies in Termite Control", Bulletin, 1922, pp. 1-20, Bulletin No. 204, New Hampshire College of Agriculture and the Mechanic Arts, USA.

U.S. Department of Agriculture, "Insect Control in Flour Mills", Handbook, 1958, pp. 23-25, Agriculture Handbook No. 133, U.S. Government Printing Office, USA.

(Unknown), "The Way Things Work", 1967, pp. 248-249, 262-265, Simon & Schuster, USA.

R. Elsworth, "Treatment of Process Air for Deep Culture", Book, 1969, pp. 129-135, vol. 1, Chapter 4, Academic Press Inc., London and New York.

David A. Sterling, C. Clark, and S. Bjornson, "The Effect of Air Control Systems on the Indoor Distributions of Viable Particles", Study, 1982, pp. 409-414, Environment International, vol. 8, Pergamon Press, Ltd., USA.

Kenneth O. Sheppard, "Heat Sterilization (Superheating) as a Control for Stored-Grain Pests in a Food Plant", Book, 1984, pp. 193-200, American Association of Cereal Chemists, USA.

Charles Forbes and Walter Ebeling, "Use of Heat for Elimination of Structural Pests", Newsletter, 1987, pp. 1-5, vol. 9, Issue 8, IPM Practitioner, USA.

Walter Ebeling, Charles F. Forbes and Sandra Ebeling, "Heat Treatment for Powderpost Beetles", Newsletter, 1989, pp. 1-4, vol. 11, Issue 9, IPM Practitioner, USA.

Stewart Brand and Richard Kadrey, "The Chronicle Whole Earth Catalog Briefing: Safe Homes/The Toxic-Free House", Article, 1991, pp. 1-3, San Francisco Chronicle, USA.

David W. Bearg, "Indoor Air Quality and HVAC Systems", Book, 1993, pp. 1-209, CRC Press, USA.

Paul Stamets, "Growing Gourmet and Medicinal Mushrooms", Book, 1993, pp. 171-173, Ten Speed Press, USA.

Walter Ebeling, "The Thermal Pest Eradication System for Structural Pest Control", Newsletter, 1994, pp. 1-7, vol. 16, Issue 2, The IPM Practitioner, USA.

M. Nicholson and W. Von Rotberg, "Controlled Environment Heat Treatment as a Safe and Efficient Method of Pest Control", Symposium, 1996, pp. 263-265, Thermo Lignum UK Ltd., UK.

Lisa G. Neven and Elizabeth J. Mitcham, "CATTS (Controlled Atmosphere/Temperature Treatment System): A Novel Tool for the Development of Quarantine Treatments", Research, 1996, pp. 56-59, American Entomologist, USA.

Jerry Heaps, "Heat for Stored Product Insects", Newsletter, 1996, pp. 18-19, vol. 18, Issues 5-6, The IPM Practitioner, USA.

David Pinniger, "Insect Control With The Thermo Lignum Treatment", Newsletter, 1996, No. 59, Conservation News, UK.

(Unknown), "Dri-Eaz Owner's Manual for Dri-X AirChanger", Manual, 1997, pp. 1-14, Dri-Eaz Products, Inc., USA.

John Gladstone and W. David Bevirt, "HVAC Testing, Adjusting, and Balancing Manual", Manual, 1997, pp. 94-101, 167-169, 172-175, 287-301, Third Edition, McGraw-Hill, USA.

U.S. Army Center for Health Promotion and Preventive Medicine, "Procedures for Thermal Control of Cockroaches in Army Food Service Facilities", Manual, 1997, pp. 1-1 thru H-1, USACHPPM Technical Guide No. 208, U.S. Government, USA.

Walter Ebeling, "Expanded Use of Thermal Pest Eradication (TPE)", Newsletter, 1997, pp. 1-8, vol. 19, Issue 8, The IPM Practitioner, USA.

R. Joseph Woodrow and J. Kenneth Grace, "Cooking Termites in the Aloha State", Article, 1997, pp. 1-3, Advanstar Communications Inc., USA.

Michael K. Rust and Donald A. Reierson, "Temperature Sensitivity in Insects and Application in Integrated Pest Management", Book, 1998, pp. 179-200, Westview Press, USA.

Brian C. Zeichner, Alfred L. Hoch and Donald F. Wood, Jr., "Heat and IPM for Cockroach Control", Newsletter, 1998, pp. 1-6, vol. 20, Issue 2, The IPM Practitioner, USA.

William Quarles, "Pest Control Operators and Heat Treatment", Newsletter, 1994, p. 8, vol. 16, The IPM Practitioner, USA.

Internet printout of "Preventing IAQ Problems at their source: Maintenance and Housekeeping", (Jan. 9, 2002), Areias LLC, USA.

(Unknown), "Atlas Owner's Manual & Parts List", manual, 2008, 14 pages, EDIC, USA.

Michael D. Geyer, "Benefits of Dry Heat to Clean Structures of Biological Contamination and Improve Indoor Air Quality (IAQ)", article, 2002, 6 pages, SCS Engineers, USA.

Alan Forbess, "Turning Up the Heat: New Remediation Process for Water Damage Could Save Insurers 'Billions'", magazine, 2006, pp. 46 & 48, Canadian Underwriter, Canada.

Alan Forbess, "Heat Treatment Method Provides Water Damage/Mold Relief", journal, 2006, 3 pages, vol. 54, No. 5, Claims, USA.

Michael Geyer, "Mold Remediation with Heat", magazine, 2006, 3 pages, ICS Cleaning Specialist, USA.

(Unknown), "Project Watch: New Weapons in the War Against Mold", magazine, 2006, 4 pages, Multifamily Trends, USA.

Megan Headley, "Some Like It Hot: How Heat Has Become a Tool for Mold Remediation", magazine, 2006, pp. 20-22 & 24, Mold & Moisture Management Magazine, Key Communications, Inc., USA.

Mike Geyer, "Structural Pasteurization: Mold Remediation With Heat", magazine, 2006, 4 pages, Building Services Management, USA.

(Unknown), "New Heat Treatment Process Used for Mold Removal", website, 2006, pp. 1-3, www.tradelineinc.com, USA.

Michael D. Geyer, "Benefits of Dry Heat to Clean Structures of Biological Contamination and Improve Indoor Air Quality (IAQ)", website, pp. 1-9, Precision Environmental, Inc., www.precisionenv.com, USA.

(Unknown), "Stop Mold With Heat", website, pp. 1-2, Precision Environmental, Inc., www.precisionenv.com, USA.

Joe McLean, "The Facts About Mold and Indoor Air Quality Using the New 'ThermaPure' Heat Treatment: Guide for Property Managers", manual, 2007, pp. 1-15, Alliance-Environmental Group, Inc. (Joe McLean), USA.

(Unknown), "Moisture Control, Mold, and the Science Within the Building Envelope", website, 2006, pp. 1-4, www.amazon.com, USA.

(Unknown), "Heat—Another Effective Tool in Your Pest Control Toolbox", manual, 148 pages, Thermal Remediation from TempAir, USA.

Anthony Manton, "Complex Solutions Made Simple", manual, 1988, pp. 1-49, Deep Sea Electronics PLC, UK.

(Unknown), "Operation Manual for EBB-40KW Trailer Package", manual, pp. 1-8, Thermal Remediation from TempAir, USA.

(Unknonwn), "Thermal Pest Management Chamber for Heat Treatment (H.T.) Process", website, 2001, 5 pages, www.pestheat.com, Pest-Heat, USA.

(Unknown), "Bed Bug: Heat Treatment Equipment and Application Training", manual, 12 pages, Thermal Remediation from TempAir, USA.

(Unknown), "EBB-115V Hotel Package", catalog, 2 pages, Thermal Remediation from TempAir, USA.

(Unknown), "Thermal Remediation Pest Control Training Course", manual, 2010, pp. 1-24, Temp-Air, USA.

Michael R. Linford and William Currie, "Bedbugs Put the Bite on Hotel Business", article, 2006, 3 pages, Asian American Hotel Owners Association, USA.

Lisa Lupo, "Treating With Heat", article, 2008, 4 pages, Pest Management, USA.

(Unknown), "Benefits of Being a ThermaPureHeat Licensee", handbook, 2005, pp. 1-39, E-Therm, Inc., USA.

Ole Dosland, Bhadriraju Subramanyam, Ken Sheppard and Rizana Mahroof, "Temperature Modification for Insect Control", book, pp. 89-102, Chapter 10 of Insect Management for Food Storage and Processing, AACC International, USA.

(Unknown), "ThermaPure, Inc. Receives New U.S. Patent for the Use of Heat Technology for Bed Bugs", 2010, article, 2 pages, ThermaPure, Inc., USA.

(Unknown), "Aggreko Heats Up the Food Industry", article, 1999, 1 page, Aggreko Inc., USA.

Alan K. Dowdy and Paul G. Fields, "Heat Combined with Diatomaceous Earth to Control the Confused Flour Beetle (Coleoptera: Tenebrionidae) in a Flour Mill", journal, 2002, pp. 11-22, Journal of Stored Products Research 38, Elsevier Science Ltd., USA.

Bhadriraju Subramanyam and David W. Hagstrum, "Inert Dusts", book, 2000, pp. 321-380, Chapter 12 of Alternatives to Pesticides in Stored-Product IPM, Kluwer Academic Publishers, USA.

Paul G. Fields, "Diatomaceous Earth: Advantages and Limitations", symposium, pp. 781-784, vol. 1, Proceedings of the 7th International Working Conference on Stored-Product Protection, Agriculture and Agri-Food Canada, Cereal Research Centre, Canada.

(Unknown), "Diatomaceous Earth (DE)", website, 2000-2007, 6 pages, The Bluebird Box—Best of Bluebird Mailing Lists Classified, Audubon Society of Omaha, USA.

(Unknown), "Model EBB-115V Thermal Treatment Heater Operator's Manual", manual, pp. 1-15, Thermal Remediation Division, Temp-Air, Inc., USA.

(Unknown), "Model EBB-460 Room Thermal Treatment Heater Operator's Manual", manual, pp. 1-14, Thermal Remediation Division, Temp-Air, Inc., USA.

(Unknown), "Temp-Heat THP-1400, 2000, 3000, 4000 and 4500: Gas, Direct-Fired Temporary Heater Installation and Service Manual", manual, 2007, pp. 1-26, TempAir, Rupp Industries, Inc., USA.

(Unknown), "Temp-Heat THP-500HT: Gas, Direct-Fired Temporary Heater Installation and Service Manual", manual, 2002, pp. 1-17, TempAir, Rupp Industries, Inc., USA.

(Unknown), "Point Sensor Temperature 3006-21 Installation and Operation Instructions", manual, 3 pages, Point Six Wireless, USA.

Albert C. Apt, "A Study of the Role of Vacuum Cleaning in the Control of Insects in Flour Mills", article, 1955, pp. 5-7, vol. 20, No. 8, Milling Production, USA.

(Unknown), "C-2000 Operating Manual", manual, 7 pages, Tri-Dim Filter Corp., USA.

George A. Dean, "Heat As a Means of Controlling Mill Insects", journal, 1913, pp. 142-161, vol. 4, Journal of Economic Entomology, USA.

George A. Dean, "Further Data on Heat As a Means of Controlling Mill Insects", journal, 1911, pp. 40-55, vol. 6, Journal of Economic Entomology, USA.

(Unknown), "Portable Industrial Unit Blower Air Heater Type DRA: Installation, Operation and Renewal Parts Identification", manual, 2002, pp. 1-6, Chromalox, Inc., USA.

(Unknown), "Temp-Heat ETHP-100: Electric Construction Heaters Installation and Service Manual", manual, pp. 1-11, TempAir, Rupp Industries, Inc., USA.

(Unknown), "Temp-Heat ETHP-1500 and ETHP-1500 Electric Construction Heaters Installation and Service Manual", manual, 1998, pp. 1-15, TempAir, Rupp Industries, Inc., USA.

(Unknown), "Remote Monitoring Wireless Sensor Product Families", catalog, 9 pages, Point Six Wireless, LLC, USA.

Walter Ebeling, "Heat and Silica Aerogel are Synergistic", article, pp. 11-12, vol. 16, IPM Practitioner, USA.

Jody Gangloff-Kaufmann and Jill Shultz, "Bed Bugs are Back! An IPM Answer", article, 2003, pp. 1-5, NYS Integrated Pest Management Program, USA.

(Unknown), "What Is Integrated Pest Management", article, 1997, pp. 3-8, Chapter 1, USEPA, Document #909-B-001 by the Bio-Integral Resource Center, USA.

C.L. Marlatt, "The Bedbug", bulletin, 1916, 17 pages, Farmer's Bulletin No. 754, U.S. Department of Agriculture, USA.

(Unknown), "Understanding the TPE Process", manual, 1999, 106 pages.

Mark Mire, "The History of Heat Sterilization for Pest Control", article, 1996, 107 pages, Aggreko, Inc., USA.

(Unknown), "Frequently Asked Questions About Bed Bugs, Their Bites, and How to Kill and Get Rid of Them", website, 2011, 6 pages, ThermaPure, Inc., USA.

G.A. Dean, "Heat for Mill Insects," Journal of Economic Entomology, 1913, pp. 40-55, vol. 6, Journal of Economic Entomology Publishing Co., Concord, New Hampshire.

Gary L. Servais, "Heat Sterilization Project", Journal, 1996, 60 pages, Brown & Williamson Tobacco Corporation, USA.

William Quarles, "Diatomaceous Earth for Pest Control", article, 1992, 16 pages, vol. XIV, No. 5/6, The IPM Practitioner, USA.

J. Coombs and K.E. Hall, "Dictionary of Biological Control and Integrated Pest Management", dictionary, 1998, 3 pages, CPL Scientific Publishing Services Limited, UK.

David Cain, "In Bed Bugs We Trust Inc. The Bed Bug University Summit", website, 2011, 2 pages, Pest Magazine, UK.

McGregor Pearce, "Mold", article, 50 pages.

Ernie Storrer, "The Drying Pie", article, 8 pages, Injectidry Systems, Inc., USA.

Michael D. Geyer, "Mold Is Not the Problem", article, 5 pages, SCS Engineers, USA.

Mike Geyer, "Mold Remediation With Heat—Does a Better Job!", article, 5 pages, SCS Engineers, USA.

Michael D. Geyer and Kenneth V. La Conde, "Toxic Mold Is Not the Problem", article, pp. 1-5, SCS Engineers, USA.

G.B. B Wickramanayake, "Decontamincation Technologies for Release from Bioprocessing Facilities", article, 1990, pp. 447-463, vol. 19, Issue 5, Taylor & Francis Publisher, UK.

(Unknown), "Guidelines on Assessment and Remediation of *Stachybotrys atra* in Indoor Environments", based on panel discussion, 11 pages, 1993, New York, NY, USA.

P.R. Morey, "Microbiological Contamination in Buildings: Precautions During Remediation Activities", article, pp. 171-178, Clayton Environmental Consultants, USA.

Eckard Johanning, Philip R. Morey and Mark Goldberg, "Remedial Techniques and Medical Surveillance Program for the Handling of Toxigenic *Stachybotrys atra*", article, 1993, vol. 4, pp. 311-316, Proceedings of Indoor Air, USA.

Pete Consigli, "Contaminated Crawl Spaces: the Good, the Bad, and the Ugly", symposium, 1996, 6 pages, ASCR 50th Convention, USA.

(Unknown), "Environmental Report #1", report, 1996, 9 pages, Safe Environments Home & Office Testing Services, USA.

James E. Holland and John Banta, "Developing Protocols and Technical Specifications: Chapter 1—Introduction", book, 1998, 10 pages, Restoration Hygiene Institute, USA.

James E. Holland, "Developing Protocols and Technical Specifications: Chapter 2—Project Planning", book, 1998, 8 pages, Restoration Hygiene Institute, USA.

James E. Holland, "Developing Protocols and Technical Specifications: Chapter 3—Containment Strategy", book, 1998, 32 pages, Restoration Hygiene Institute, USA.

James E. Holland, "Developing Protocols and Technical Specifications: Chapter 4—Safety Issues", book, 1998, 9 pages, Restoration Hygiene Institute, USA.

James E. Holland, "Developing Protocols and Technical Specifications: Chapter 5—Job Set Up Work Area Preparation", book, 1998, 28 pages, Restoration Hygiene Institute, USA.

James E. Holland, "Developing Protocols and Technical Specifications: Chapter 6—Work Procedures", book, 1998, 39 pages, Restoration Hygiene Institute, USA.

James E. Holland, "Developing Protocols and Technical Specifications: Chapter 7", book, 1998, 5 pages, Restoration Hygiene Institute, USA.

David Bierman, "Microbial Contamination", report, 12 pages, Safe Environments Home & Office Testing Services, USA.

Joseph W. Lstiburek, "Mold, Moisture & Indoor Air Quality: A Guide for Designers, Builders, and Building Owners—Introduction", book, 1994, 14 pages, Building Science Corporation, USA.

Joseph W. Lstiburek, "Mold, Moisture & Indoor Air Quality: A Guide for Designers, Builders, and Building Owners—Chapter 1: People, Buildings, and the Environment", book, 1994, pp. 7-20, Building Science Corporation, USA.

Joseph W. Lstiburek, "Mold, Moisture & Indoor Air Quality: A Guide for Designers, Builders, and Building Owners—Chapter 2: HVAC Systems and Air Quality Problems", book, 1994, pp. 21-50, Building Science Corporation, USA.

Joseph W. Lstiburek, "Mold, Moisture & Indoor Air Quality: A Guide for Designers, Builders, and Building Owners—Chapter 3: Moisture Movement and Relative Humidity", book, 1994, pp. 51-62, Building Science Corporation, USA.

Joseph W. Lstiburek, "Mold, Moisture & Indoor Air Quality: A Guide for Designers, Builders, and Building Owners—Chapter 4: Microbial Contamination", book, 1994, pp. 63-68, Building Science Corporation, USA.

Joseph W. Lstiburek, "Mold, Moisture & Indoor Air Quality: A Guide for Designers, Builders, and Building Owners—Chapter 5: Cold Climate Mold, Mildew and Condensation", book, 1994, pp. 69-82, Building Science Corporation, USA.

Joseph W. Lstiburek, "Mold, Moisture & Indoor Air Quality: A Guide for Designers, Builders, and Building Owners—Chapter 6: Warm Climate Mold, Mildew and Condensation", book, 1994, pp. 83-112, Building Science Corporation, USA.

Joseph W. Lstiburek, "Mold, Moisture & Indoor Air Quality: A Guide for Designers, Builders, and Building Owners—Chapter 7: Vapor Diffusion Retarders, Air Retarders and Insulating Sheathings", book, 1994, pp. 113-128, Building Science Corporation, USA.

Joseph W. Lstiburek, "Mold, Moisture & Indoor Air Quality: A Guide for Designers, Builders, and Building Owners—Chapter 8: Case Studies", book, 1994, pp. 129-244, Building Science Corporation, USA.

Michael A. Berry, "Protecting the Built Environment: Cleaning for Health", book, 1993, 84 pages, Tricomm 21st Press, USA.

(Unknown), "ASHRAE Handbook: 1983 Equipment Volume", handbook, 1983, 78 pages, American Society of Heating, Refrigerating and Air-Conditioning Engineers, Inc., USA.

(Unknown), "1996 ASHRAE Handbook: Heating, Ventilating, and Air-Conditioning—Systems and Equipment", handbook, 1996, 194 pages, American Society of Heating, Refrigerating and Air-Conditioning Engineers, Inc., USA.

(Unknown), "ASHRAE Handbook: 1982 Applications", handbook, 1982, 84 pages, American Society of Heating, Refrigerating and Air-Conditioning Engineers, Inc., USA.

(Unknown), "ASHRAE Handbook: 1984 Systems", handbook, 1984, 104 pages, American Society of Heating, Refrigerating and Air-Conditioning Engineers, Inc., USA.

(Unknown), "1995 ASHRAE Handbook: Heating, Ventilating, and Air-Conditioning Applications", handbook, 1995, 232 pages, American Society of Heating, Refrigerating and Air-Conditioning Engineers, Inc., USA.

(Unknown), "The Dehumidification Handbook", handbook, 1982, 67 pages, The Cargocaire Engineering Corporation, USA.

(Unknown), "The Dehumidification Handbook", handbook, 1990, 2nd Ed., 153 pages, Munters Cargocaire, USA.

(Unknown), "Design Considerations for Toxic Chemical and Explosives Facilities", symposium, 1987, 33 pages, American Chemical Society, USA.

Seymour S. Block, "Disinfection, Sterilization, and Preservation", 3rd Ed, book, 1983, 160 pages, Lea & Febiger, Philadelphia, PA, USA.

W.A. Murray, A.J. Streifel, T.J. O'Dea, F.S. Rhame, "Ventilation for Protection of Immune Compromised Patients", journal, 1988, pp. 1185-1191, vol. 94, USA.

John R. Girman, Leon E. Alevantis, George C. Kulasingam, Myrto X. Petreas, and Lurance M. Webber, "The Bake-Out of an Office Building: A Case Study", study, 1989, Environmental International, vol. 15, pp. 449-453, Pergamon Press, USA.

Ernie Storrer, "Mold & Trapped Moisture", article, 1997, 2 pages, Cleaning and Restoration, Injectidry Systems, Inc., USA.

(Unknown), "Structural Drying School Handbook", handbook, pp. 1-82, American Drying Institute, USA.

Chuck Dewald, "Chuck Dewald's Vortex Drying System School Study Guide", handbook, pp. 1-10, Vortex Drying System, USA.

(Unknown), "The 'Mobile Hands-On' Water Damage Restoration Technician School: Interactive Student Manual", manual, 2000, 292 pages, Aspire Educational Institute & Conference Centre, Costa Group, Inc., USA.

Clifford B. Ziotnik, "Microban Systems, Inc. Water Restoration Technology Manual", manual, 2002, 96 pages, Microban Systems, Inc., USA.

Michael A. Pinto and David Janke, "Fungal Contamination: A Comprehensive Guide for Remediation", handbook, 2001, 329 pages, Wonder Makers Environmental, Inc., USA.

Bill Lundquist et al., "Assessment, Cleaning, and Restoration of HVAC Systems", manual, 2006, 52 pages, National Air Duct Cleaners Association (NADCA), USA.

(Unknown), "A Brief Guide to Mold in the Workplace", bulletin, 2010, 51 pages, Office of Science and Technology Assessment, USA.

(Unknown), "Mold Remediation in Schools and Commercial Buildings", manual, 2001, 70 pages, U.S. Environmental Protection Agency, USA.

Joseph A. Hughes, "Indoor Environmental Contractor Program: Microbial Remediation Supervisor", manual, 2003, 231 pages, IAQ Training Institute LLC, USA.

William Quarles, "Thermal Pest Eradication in Structures", newsletter, 2006, 8 pages, vol. 28, Issue 5/6, The IPM Practitioner, USA.

George A. Dean, "Further Data on Heat as a Means of Controlling Mill Insects", journal, 1913, pp. 40-55, vol. 6, Journal of Economic Entomology Publishing Co., USA.

(Unknown), "Standard and Reference Guide for Professional Water Damage Restoration (IICRC S500)", manual, 1994, 360 pages, Institute of Inspection, Cleaning and Restoration (IICRC), USA.

(Unknown), "Standard and Reference Guide for Professional Mold Remediation (IICRC S520)", manual, 2003, 239 pages, Institute of Inspection, Cleaning and Restoration (IICRC), USA.

(Unknown), "Electric Thermal Energy System Operator's Manual (120 Volt)", manual, 2010, 44 pages, Bridgepoint Systems, USA.

(Unknown), "Electric Thermal Energy System Operator's Manual (240 Volt)", manual, 2009, pp. 1-4, 7-39, Bridgepoint Systems, USA.

* cited by examiner

SYSTEM AND PROCESS FOR REMOVING OR TREATING HARMFUL BIOLOGICAL AND ORGANIC SUBSTANCES WITHIN STRUCTURES AND ENCLOSURES

RELATED APPLICATION

This application is a continuation-in-part of U.S. application Ser. No. 10/371,826, filed Feb. 20, 2003 now U.S. Pat. No. 8,221,678, which is a continuation-in-part of U.S. patent application Ser. No. 10/313,901, filed Dec. 5, 2002 now abandoned, and which further claims priority from U.S. Provisional Application Ser. Nos. 60/358,222 and 60/358,223, both filed Feb. 20, 2002.

BACKGROUND OF THE INVENTION

The present invention relates to methods of sanitizing structures, buildings, passenger occupiable vehicles, and other enclosed or enclosable spaces. More particularly, the present invention relates to a system and method for killing and removing insects, dust mites and their allergens, bacteria, viruses, fungi, molds, and volatile organic compounds from such enclosures.

A large number of methods have been developed for killing insects, such as termites, in buildings. The most widely used method is tenting the building, then filling the building with a toxic gas for a period of time sufficient to kill termites or other selected insects. This method is effective for killing termites and other insects. However, this method generally requires 12 hours to be effective, requiring building occupants to move out and businesses to be closed for approximately a three day period to insure proper venting of toxic material and/or gas. Tenting the building with heavy tarpaulins requires workers to walk and arrange the tarpaulins on the roof, often damaging the roof system. Food and medications must be placed in sealed containers or removed. Generally the entire building must be treated, even if the infestation is localized.

Techniques of varying effectiveness have been developed using heated air or very cold air to kill termites and other organisms. Typical of these are the methods disclosed by Charles Forbes in U.S. Pat. No. 4,817,329, and Hedman et al. in U.S. Pat. No. 6,327,812 in which wood destroying insects, e.g., termites, are killed by applying a heated gas, such as heated air, to wooden surfaces or the like until the core of wooden structures is heated to a temperature typically about 120° F. to 135° F. Temperatures for killing other insects are said to be surprisingly close to this range. This method has been found to be very effective for killing termites. Another alternative to the toxic gas method is disclosed by James J. Chaudoin, et al. in U.S. Pat. No. 4,958,456, in which insects, e.g., roaches, fleas and beetles, are killed by a treatment of building spaces with boric acid and heat. However, the methods disclosed in the Forbes and Hedman et al. patents are quite complex in the preparation of the building. An enclosing tent structure must be formed around the structure to be decontaminated. Tenting the building with heavy tarpaulins requires workers to walk and arrange the tarpaulins on the roof, often damaging the roof system.

Also, these methods, using the described temperatures, is not effective for other organisms, such as bacteria, viruses, fungi, and molds such as, but not limited to, *aspergillus oryzae, aspergillus terreus, aspergillus versicolor, cladosporium hergbarum, stachybotrys chartarum, penicillium aurantiogriseum, pencillium chrsogenum, pencillium gladrum* and *fusarium oxysporum*. Further, many such fungi, molds and the like are a serious health hazard even when dead. Many people are allergic to the dust-like remains and residue, i.e., allergens, of these organisms that can also cause serious health problems. This is a particular problem to persons suffering from asthma, bronchitis, pneumoconious and other respiratory ailments, and is a common contributing factor to sick building syndrome (SBS).

It is also well-known that the heated air causes certain molds, fungi, etc. to sporulate, thus releasing spores into the structure and thus dispersing the harmful biological agents and possibly contaminating the structure to a greater degree than originally presented. The use of positive pressure within the structure, as described in Forbes and Hedman et al., further increase the likelihood that the biological contaminants will be dispersed throughout the structure. Forbes and Hedman et al. also disclose that the heated air can be vented from open windows and the like. However, when treating a contaminated building having harmful viruses, toxic molds, etc., it is not desirable to release such contagions into the air.

Volatile organic compounds (VOCs) have also been implicated as a possible cause of SBS. VOCs can originate from a variety of sources. Commercial examples include by-products of printing shop operations, office machine repairs, blueprint production, photographic processing and food service operations. In residences, such VOCs can include hobbyist products, cosmetics, perfumes, personal hygiene products, aerosol sprays, tobacco smoke, pet urine and even small emissions from the bodies of the occupants. Off gassing of VOCs is often a common by-product of various building/construction materials, for example paints, adhesives, plastics, carpeting, etc.

Such VOCs are implicated with SBS for mostly two reasons. First, the health effects from exposure to VOCs are consistent with SBS, ranging from irritant effects such as unpleasant odors and mucous membrane irritation, through general systemic effects such as fatigue, nausea, and difficulty concentrating. In addition, they may be of importance because some of them have been shown to have carcinogenic or adverse reproductive effects. Second, indoor concentrations of VOCs, particularly in new buildings, are often greatly elevated with respect to outdoor VOC concentrations. In fact, indoor VOC concentrations have typically been found to be two to ten times higher then outdoor concentrations, and indoor concentrations as much as 100 times higher than outdoor concentrations have been reported in new buildings.

Passenger occupiable vehicles, such as trains, buses, airplanes, etc. also include building/construction materials which are known to off gas VOC's. Also, the fuel, oil, and grease fumes and odors can infiltrate the passenger compartments of such vehicles and build-up within the seats, carpets, etc. over time. Due to the great number of people regularly traveling in such vehicles, there is an increased chance of coming into contact with contagious bacterium or viruses that can cause illness. Other organisms, such as fungi, and toxic molds can also be potentially found in such vehicles. As the company owning such vehicles necessarily must keep the vehicles running nearly constantly in order to realize the expected profit, such vehicles are rarely cleaned thoroughly. Even if the surfaces are superficially vacuumed and wiped down, there still remain live and dead organisms such as lice, mites, fungi, toxic molds, bacterium, viruses, VOCs, oxidized odors, and potentially insects which may have infested the vehicle, particularly those where food is prepared or served.

There are also instances when personal articles and small pieces of furniture need to be treated. For example, bedding and mattresses over time can accumulate a large amount of allergens, in the form of dust mites and their allergens, etc. Furniture may also experience water damage, causing fungi and toxic molds to grow thereon. These articles may also need to be treated for contagious bacterium or viruses that can cause illnesses.

Accordingly, there is a need for a system and method for killing and removing biological organisms and reducing odors and volatile organic compounds in enclosures such as commercial and residential buildings, boats, vehicles and portable containers. Such a method should be non-toxic and performed in a relatively short amount of time. Such a method should also effectively kill and remove a large proportion of the dead organisms and substantially reduce volatile organic compounds. The present invention fulfills these needs and provides other related advantages.

SUMMARY OF THE INVENTION

The present invention resides in a process for removing or treating harmful biological and organic substances from an enclosure, such as a building or vehicle or pre-fabricated treatment chamber device. The method of the present invention is non-toxic and can be performed in a relatively short amount of time while effectively killing and removing a large proportion of dead organisms and substantially reducing volatile organic compounds.

The process generally comprises enclosing a selected area which is contaminated. The area may comprise at least a portion of a contaminated building or a vehicle. Alternatively, the enclosed area comprises a treatment chamber into which are placed contaminated objects. Air inlet and air outlet ducts are provided to the selected area. The object or contaminated area may be physically cleaned as preparation for the treatment. Additionally a biocide, such as a borate based compound, may be applied to the contaminated area directly. Any heat-sensitive articles within the enclosed area are either removed or protected, such as with the use of mats or fans disposed adjacent to such articles.

The enclosed area is then depressurized such that air removed from the enclosed area is greater than air introduced thereto. The enclosed area is monitored to determine that sufficient depressurization has been established, such as by using a manometer or other pressure sensing device. Moisture may also be removed from the air within the enclosed area, depending upon the treatment needs.

The air within the enclosed area is then heated to a predetermined temperature to cause harmful biological or organic substances to be destroyed or migrate into the ambient air. This can be accomplished by placing and distributing heated air into the enclosed area, such as with blowers or the like. Typically, the ambient air within the enclosed area is heated to between 110° F. and 400° F. A biocide may be introduced into the heated air. Preferably, the air is aggressively moved within the enclosed area to aerosolize the biological and organic substances to facilitate their removal.

The temperature of the enclosure is monitored until the predetermined temperature is reached. Such monitoring may be accomplished with a sensor disposed outside of the enclosed area, such as at the air inlet or air outlet duct.

The contaminated area, or the air within the enclosure, may be irradiated with electromagnetic waves. Preferably, the heated air removed from the enclosed area is passed through an incinerator or filter or irradiation device to remove or destroy harmful biological or organic substances from the air.

Treatment personnel may enter the building or vehicle using protective gear to inspect the contaminated areas during treatment.

Non-heated ambient air may be directed into the enclosed area after a predetermined time of directing heated air into the enclosure, or it is determined that sufficient treatment has occurred. Preferably, the air is passed through a filter, an incinerator or an irradiation device. In one embodiment, the contaminated area may be subjected to freezing, such as by passing cold air through the enclosed area, for further treatment purposes.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings for purposes of illustration, the present invention is related to a system and method for removing harmful organic substances, such as VOCs, dust mites and their allergens, bacteria, and insects, from an enclosure.

Figure 1:
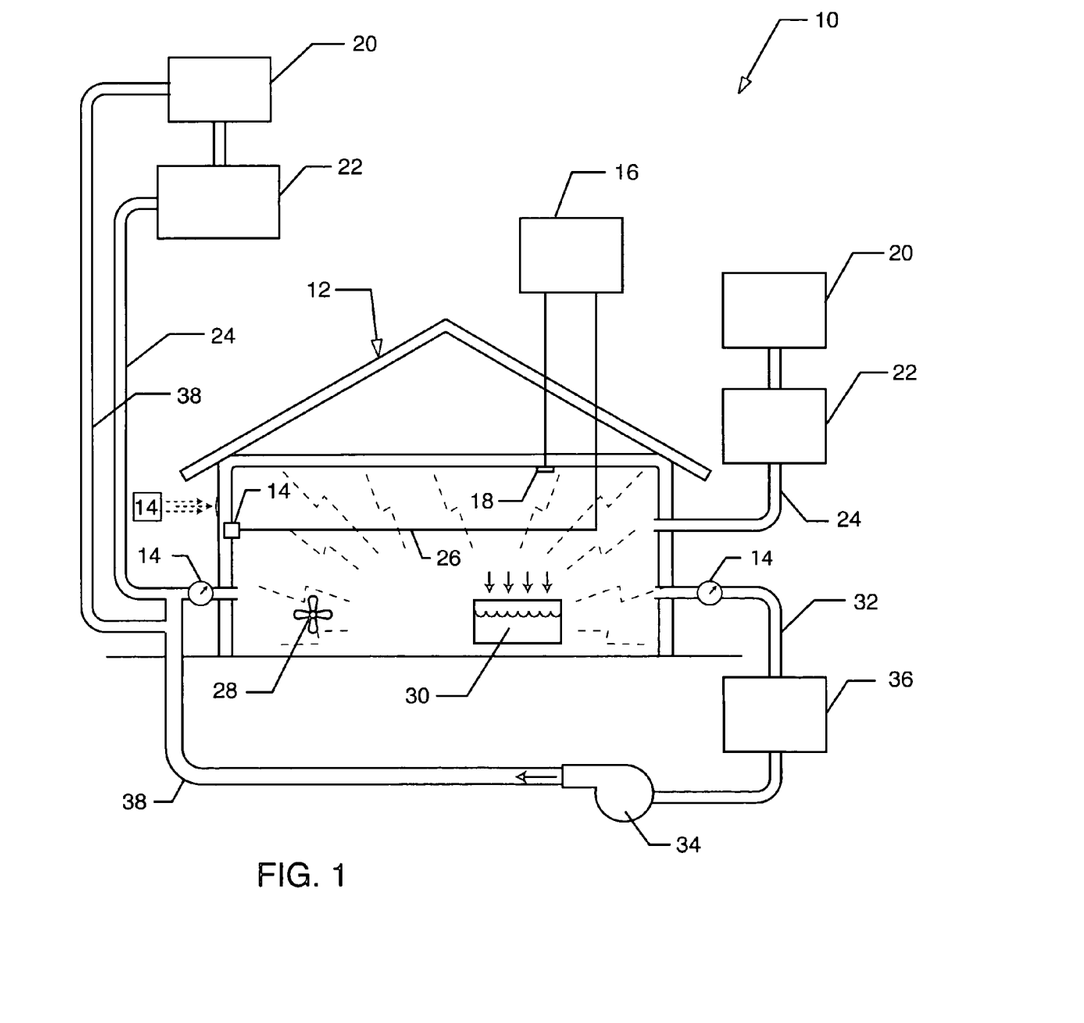
FIG. 1 is a schematic diagram showing components of the system of the present invention installed for treatment of a building.
Figure 2:
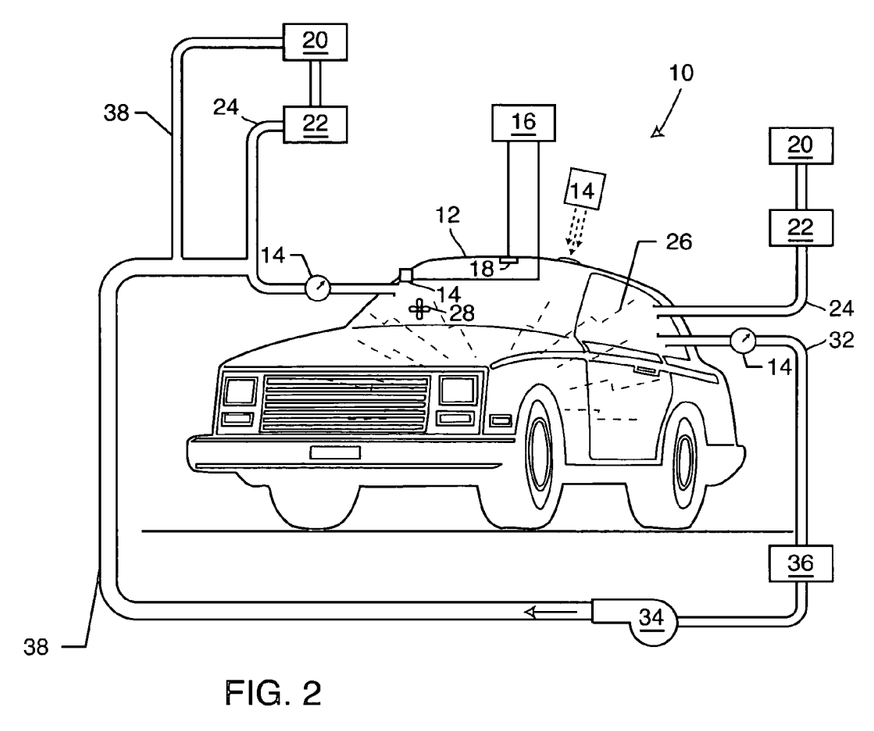
FIG. 2 is a schematic diagram showing an automobile treated in accordance with the present invention.
Figure 3:
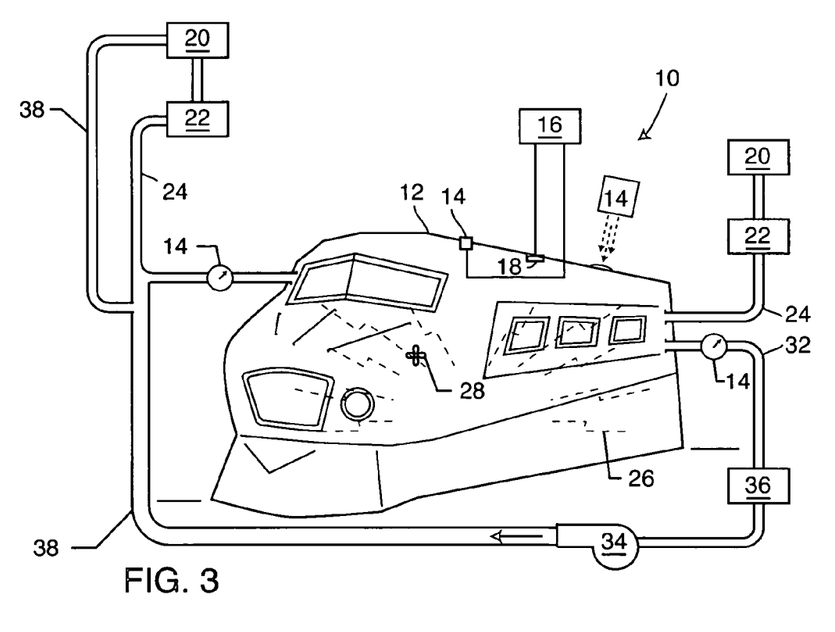
FIG. 3 is a schematic diagram illustrating a train being treated in accordance with the present invention.
Figure 4:
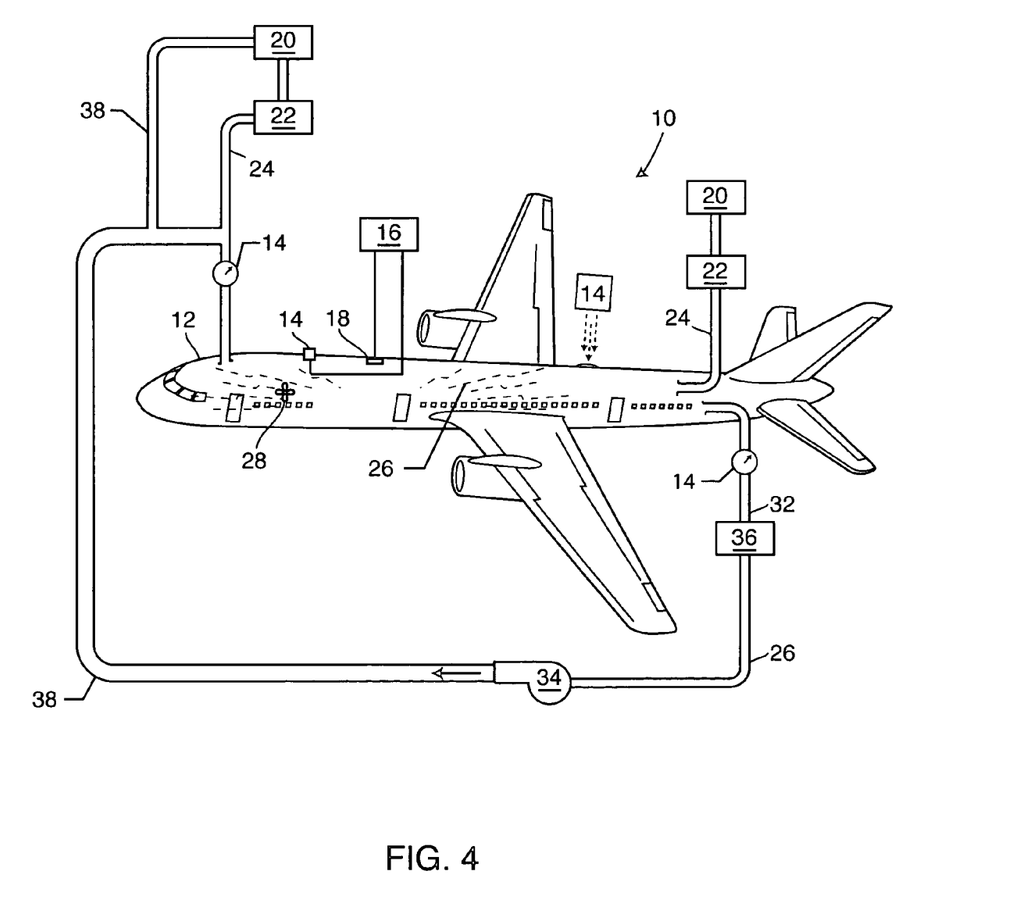
FIG. 4 is a schematic diagram of an airplane being treated in accordance with the present invention.

Referring to FIGS. 1-4, there is seen a schematic diagram showing the components of the system of the present invention, referred to generally by the reference number 10, in use treating an enclosed structure 12. The enclosed structure 12 is typically a commercial or residential building, but can also be a vehicle, such as an airplane, bus, boat, automobile, etc., as shown in FIGS. 2-4. The system of the present invention can also be used in treating objects such as the materials which are used in the construction of such structures and vehicles.

A temperature sensor 14 may be positioned within the structure to monitor the temperature of the structure 12. If the temperature sensor 14 is disposed within the structure 12, it is typically inserted into the structure 12 itself, such as by drilling a hole into a wooden beam or the like and inserting the temperature sensor 14 therein so as to monitor the temperature within the supports of the structure itself. The temperature of the structure 12 may also be monitored using an external temperature sensor 14. Such sensor may be placed on a window, for example, or, as illustrated, comprise a laser temperature sensor wherein a beam of laser light is directed at the structure and used to determine the temperature of the structure 12. As will be more fully described herein, the temperature of the structure 12 can also be monitored by monitoring the heated air at the ingress to the structure, or at the egress duct of the structure. The sensor 14 may be wired to a console 16 which displays and records the temperature of the sensor 14 in real time. Alternatively, the sensor 14 may be wireless and transmit a signal to the console 16. Typical 
sensors 14, as for way of example and not by way of limiting, include thermal couples, thermistors, or the like connected to a computer and/or a strip chart recorder console 16.

A pressure measuring device, such as a manometer 18, is positioned within the structure 12 so as to measure the internal pressure of the structure 12 during operation of the invention. As will be more fully described herein, a negative pressure is preferably established and maintained throughout the operation of the method of the present invention in order to prevent the dispersal of harmful biological and organic contaminants throughout the structure 12. The manometer 18 can be linked to the console 16 to provide the pressure information from without the structure 12.

One or more heaters 20 heat air to a predetermined temperature lethal to the organisms to be destroyed. For a more complete disinfection, the air temperature is preferably raised to at least about 110° F., with optimum results generally achieved with temperatures in the range of about 155° F. to 400° F., or higher. A biocide, having desirable characteristics enhanced by heat, may be introduced with the heated air or previously applied to contaminated areas.

Any suitable heater 20 may be used. A gas burning heating device 20, such as a conventional propane heater, is preferred as being particularly efficient in heating air. Any other heating arrangement, such as electrical devices, solar heaters, and electromagnetic radiation emitting devices, may be used if desired.

Heated air (and biocide, such as a borate-based compound, if used) from the one or more heaters 20 is directed through blower 22 (which may, if desired, be a component of the heater 20) which injects the hot air into the enclosed structure 12 through at least one inlet duct 24. Generally, a plurality of inlet ducts 24 will be used to achieve the optimum distribution of hot air throughout the enclosed structure 12. The inlet ducts 24 preferably include variable flow dampers and may be moved while the system is in operation to achieve uniform temperatures in all areas of the structure being treated, as sensed by sensor 14 and observed at console 16.

The system may also incorporate the use of a radiation emitting device which can emit microwave or infrared emitting radiation 26 to heat the air within the structure. Such a device may be used in association with the gas burning heating device, or placed within areas of the structure to heat the structure directly from within. Various spectrums may be selected so that the electromagnetic device may also serve to kill organisms, such as by emitting ultraviolet light 26 or the like. Another radiation emitting device that could be used is an electron beam emitting device, such as those offered by Electron Beams, Inc. Electron beams have been found to cleave chemical bonds or seal others, such as to disrupt a virus or bacteria's genes. Electron beams can break carbon bonds and thus sterilize the air or area or the contaminated area.

Figure 5:
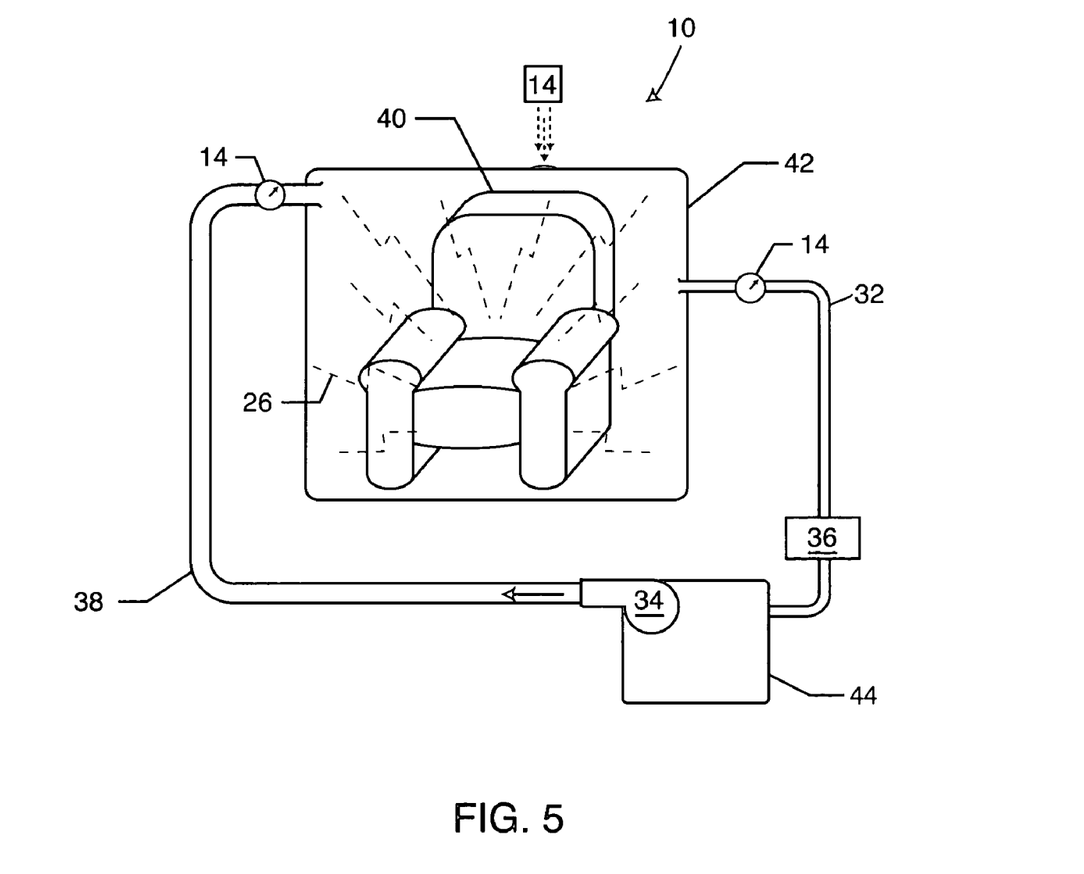
FIG. 5 is a schematic diagram illustrating a portable decontamination system used in accordance with the present invention to treat smaller objects.

Preferably, blowers 28 or fans are positioned within the structure 12 to aggressively move the air within the structure to further enhance the removal of harmful biological and organic substances by aerosolizing the biological and organic substances and aid in heat distribution. Additionally, fans may be positioned strategically within the structure 12 to selectively move the air away from predetermined heat-sensitive articles or areas of the structure in which such an elevated temperature is not desired. Typically, however, such heat-sensitive articles are removed from the structure or covered with insulation mats or the like or removed from the structure 12.

In a particularly preferred embodiment, the air which is heated and introduced into the structure can be selectively devoid of humidity and moisture as well as carbon dioxide or carbon monoxide. Accordingly, a dehumidifier 30 may be placed within one or more areas of the structure in order to remove the moisture from the air therein. The removal of moisture is particularly useful when treating for insects or toxic mold and the like. In a particularly preferred embodiment, moisture is added to air initially so as to enhance the treatment, and then remove towards the end of the process, such as using the illustrated dehumidifier 30, so that the contaminated area and structure are dry. Drying the contaminated area and structure kills the toxic mold and prevents other mold and fungus from growing in the future.

At least one outlet duct 32 is provided to allow the air to be removed from the structure 12. A blower or vacuum 34 is connected to the outlet duct 32 in order to remove air from the interior of the structure 12. Vacuum 34 may be used to depressurize the structure 12. Typically, the negative pressure or depressurization is established before the heated air is introduced into the structure 12.

The removed air may be filtered, typically utilizing a high particulate arrestance filter, ULPA filter, or the like 36 coupled with the vacuum/blower 34. Other filters such as charcoal filters or UV filters may be employed as well. The filter or air scrubber 36 removes or destroys the remains of the organisms and VOCs from the air to prevent them from reaching the environment or being re-introduced into the structure 12. Alternatively, no filters at all may be used, instead the heated air which exits through the outlet duct 32 is processed through a heat exchanger 36 which incinerates the contaminants and minimizes toxic gases.

In a particularly preferred embodiment, the filtered air is re-directed through duct 38 into the structure 12, such as by linking duct 38 with inlet 24. Such re-circulation of heated air enhances the energy and thermal efficiency of the process and decreases the overall treatment time. Additionally, it has been found that merely venting the air into the environment causes heat dilution and stratification to occur within the structure 12. Re-circulating the filtered and heated air reduces the heat dilution and stratification, and has been found to increase treatment air circulation within the containment area of the structure 12. The re-circulated air may be blended with the heat processed air as it exits the heater barrel, re-heated by the heater 20 or simply re-introduced by way of ducting into the structure 12. Preferably, the air is recirculated so that it is introduced into the heater 20, which then serves as an incinerator to destroy and burn the particles which have been removed from the enclosed area or structure.

Although the above description has been directed to rather large structures, such as residential or commercial buildings and passenger occupiable vehicles and the like, the present invention can also be applied to treatment of much smaller areas or objects. For example, a single room of a building may be treated by sealing the windows, doors, and other passageways of that particular room or area and treating such area, as described above.

There are also instances where small personal articles, such as clothing or bedding, or even furniture is required to be treated, but not the structure itself. As illustrated in FIG. 5, the present invention can be adapted for treatment of such articles 40. A common instance of treatment is the destruction or removal of allergens such as dust mite feces and the like from bedding and mattresses. Dust mite feces are known to cause mild and even severe allergic reactions in some individuals. These individuals may have headaches, runny noses, persistent coughs, etc. which is not caused by an infection, but rather allergic reaction to the allergens. The personal articles 40, in the form of bedding or the like, is placed within a portable structure 42. Such portable structure 42 may comprise a rigid and portable structure of sufficient size to treat the articles. For example, the back of a van may be converted into a treatment containment area. Alternatively, an inflatable bag, typically comprised of appropriate thermal material, is used. The personal articles 40 are placed within such a thermal envelope or bag 42 and heated air directed into the inlet thereof. Pressure and temperature are monitored and controlled using a device 44 attached to the portable structure 42. Preferably, the heated air which is removed is re-circulated, as described above. If toxic molds or fungi are of a concern, the air temperature may be reduced over time to prevent sporulation and the like.

The system of the present invention can also be used to dry and preshrink wood components of structures before or during the construction process. It is not uncommon in the building industry to have components, such as wood beams and the like, which become wet due to adverse weather conditions during the construction process. Moisture within the structure can allow toxic mold and funguses to grow therein. Accordingly, the present invention can be used to dry these components during the construction process. The same concept can be used for other devices, structure and even vehicles.

The system of the present invention can also be used in conjunction with the encapsulation or enclosure of soil which needs to be treated either in conjunction with the structure, or even completely separate from the structure. Use of portable or small treatment structures 42 can be particularly useful in such applications.

Figure 6A:
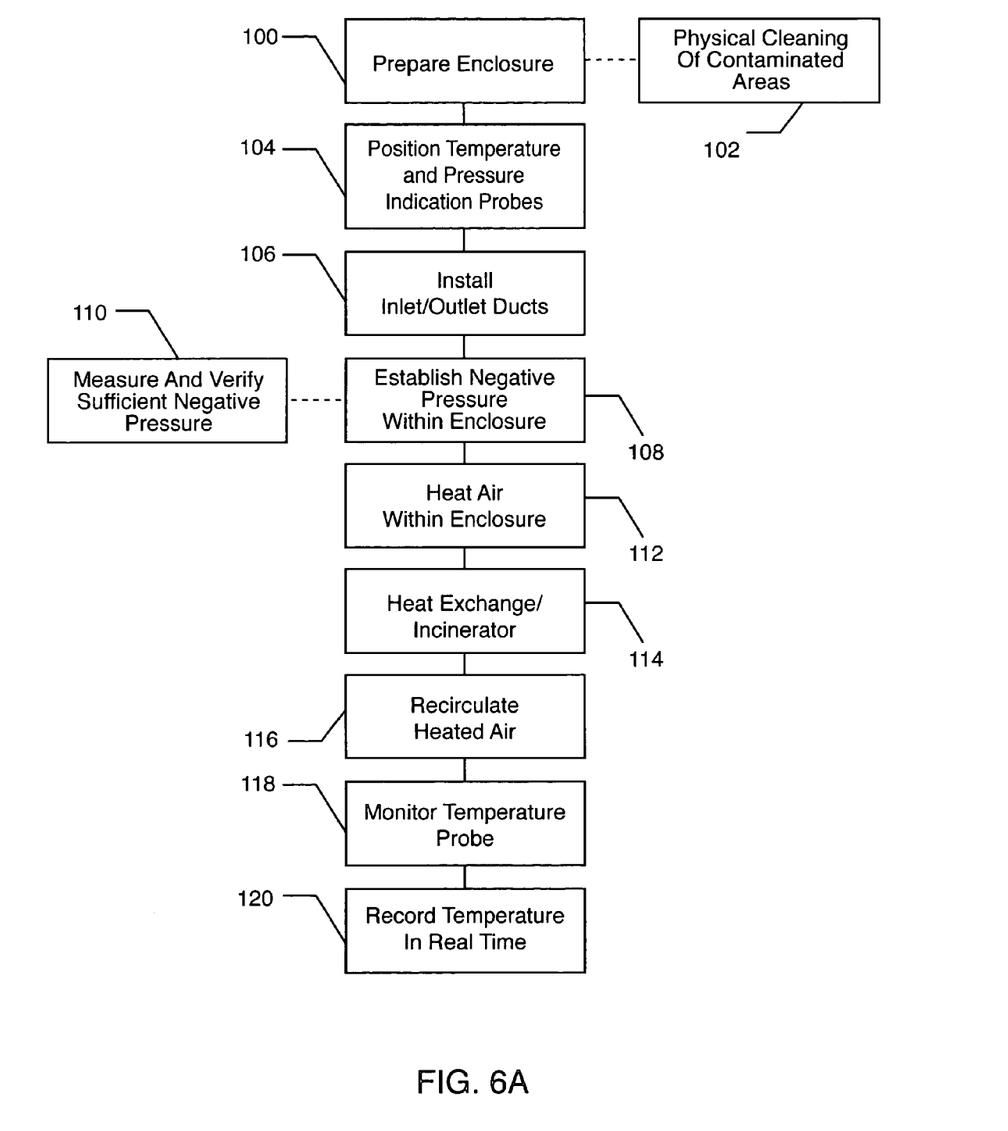
FIGS. 6A and 6B are flow diagrams illustrating the method used in accordance with the present invention.

With reference to FIG. 6A, in the operation of the system of the invention, the first step is to prepare the enclosure, as indicated in block (100). This basically involves removing all heat-sensitive items from the enclosure or, in some cases, covering heat sensitive items, such as electronic devices and plastic items, with thermal insulation material. All material that has a flash/melt point at or below the maximum temperature to be used (such as candles, lipstick, etc.) should be removed.

Typically, the preparation of the structure also includes physical cleaning of contaminated areas (102), which may be preformed while the area is under a negative pressure. This can include vacuuming, wiping, sanding, scraping, etc. of various surfaces which have been contaminated with harmful biological contaminants, such as mold, fungi or bird, rodent or insect debris, etc. Biocides may also be applied to the contaminated areas. In extreme cases, this may require the removal of carpeting, section of walls, etc. However, the invention is intended to neutralize and remove these biological and organic contaminants without requiring resort to such extreme measures.

In one embodiment, particularly when treating the structure 12 for mold and fungi, borates, and preferably boric acid, are dispersed within the structure 12 at locations, preferably, where mold and fungi are likely to be encountered. Boric acid, $H_3BO_3$, is a white crystalline, oxygen-bearing acid of boron found in certain minerals and volcanic waters or hot springs in certain mineral deposits. Boric acid, or salts of boric acid, borates, and traces of boron are necessary for growth of land plants and thus are indirectly essential for human life. In excessive quantities, however, borates may act as unselective herbicides. The most common source of boric acid is borate, sodium tetraborate or borax, which occurs naturally in salt beds. Boric acid may be obtained by treating borate with sulfuric acid. Boric acid is commonly used as a mild antiseptic for burns and surface wounds and comprises a major ingredient in eye lotions. Among its other important applications is its use as a fire retardant in fabrics. Importantly, boric acid is non-toxic to humans and animals and is ecologically benign in low concentrations.

Applying boric acid using conventional applicator methods and devices, (i.e., dusting boric acid as a conventional insecticide as dust, spraying a solution or slurry or dispersion of boric acid, etc.), coupled with heating the air within the enclosure, advantageously improves mold, fungi and pest (termite) abatement within the structure 12. The borates may be used in pre-treating contents of an enclosure, such as building materials, lumber, etc. or in post-treating such contents after application of heat.

In some instances, particularly where the contaminated area is localized, the area is sealed or encapsulated, such as by using a polymeric material which can be placed over or sprayed onto the contaminated area. Sealing the contaminated area prevents migration of any of the dead mold, spores, etc. The polymeric material or other sealant may also be applied to the soil underlying the structure to prevent moisture from extending into the structure, or also to treat mold and the like which are in the soil and not in the structural components themselves. Sealing or encapsulating such contaminated areas has been found to be particularly useful as the contaminants are localized and maintained within a certain area, yet killed due to the heat treatment. Application of boric acid or other biocides may be applied to the contaminated area prior to sealing.

Temperature indicating and pressure measuring probes 14 and 18 are placed in predetermined locations as indicated in block (104) to assure that the required temperature levels are achieved. As discussed above, the temperature probes 14 may comprise a single temperature probe within the structure itself, and preferably inserted within a wooden beam or the like of the structure. Alternatively, the temperature probe 14 is an exterior temperature probe which monitors the temperature of the structure, with the use of laser beams or other means, outside of the structure. The temperature may be monitored through the gas ingress or egress ducts 24 or 32. In some cases the probes 14 can be read directly, although preferably they are connected by wires or wireless means to the console 16, so that all probes 14 and 18 can be monitored conveniently and the data recorded in real time.

When the enclosed structure 12 is sealed, at least one inlet duct 24 and at least one outlet duct 32 are then installed as indicated in block (106). Generally, a plurality of inlet ducts 24 is preferred. Although each duct 24 may enter the enclosed structure 12 separately, the use of one inlet duct 24 connected to a manifold from which plural ducts extend to predetermined locations within the enclosed structure 12 is preferred. Ducts 24 may enter the structure 12 through any suitable opening, such as an open window or door with the remainder of the window or door blocked by a panel. In some instances, such as when treating vehicles, tenting may actually be required or desired to treat the structure 12. However, in most instances such tenting is not required.

When the components of the system 10 have been properly prepared and positioned, the desired negative pressure is established within the structure 12 (108) and the manometer or other pressure sensing device 18 is used to verify that a sufficient negative pressure is present (110). When using a self-contained portable treatment unit 42, many of these steps will be unnecessary as the components and ducts may be built into the unit 42. Typically, a negative air pressure within the structure 12 is desirable, by removing air more quickly than it is introduced, to ensure the removable of the contaminants therefrom and to promote circulation of the air. Using the pressure measuring manometer device 18, the internal pressure of the structure is measured and it is verified that sufficient depressurization is achieved (110). Often the establishment of negative pressure is performed before any heat is introduced into the structure in order to begin the removal of any loose and aerosolized contaminants, and prevent their sporulation before heat is introduced.

The air in the structure is then heated, such as by directing heated air into the inlet ducts (112) to heat the structure. As indicated above, electromagnetic devices may also be used to decontaminate the structure, or even heat the structure.

The air is then passed through a heat exchanger, wherein the air can be incinerated so as to ensure the destruction of the contaminants and any other by-products (114). As discussed above, the air may also be passed through a filter.

The heated air is then re-circulated into the inlet ducts (116). Flow of the heated air through the enclosed structure 12 may range in time from a few hours to several days to provide optimum results. During this time, the probes 14 and 18 are monitored (118) and these results recorded in real time (120) to ensure that the intended areas within the structure 12 are properly treated.

At any time during system operation, the inlet and outlet ducts 24 and 32 may be moved to assure uniform temperatures throughout the structure, as indicated by the temperature probe 14 and temperature monitoring console 16.

Figure 6B:
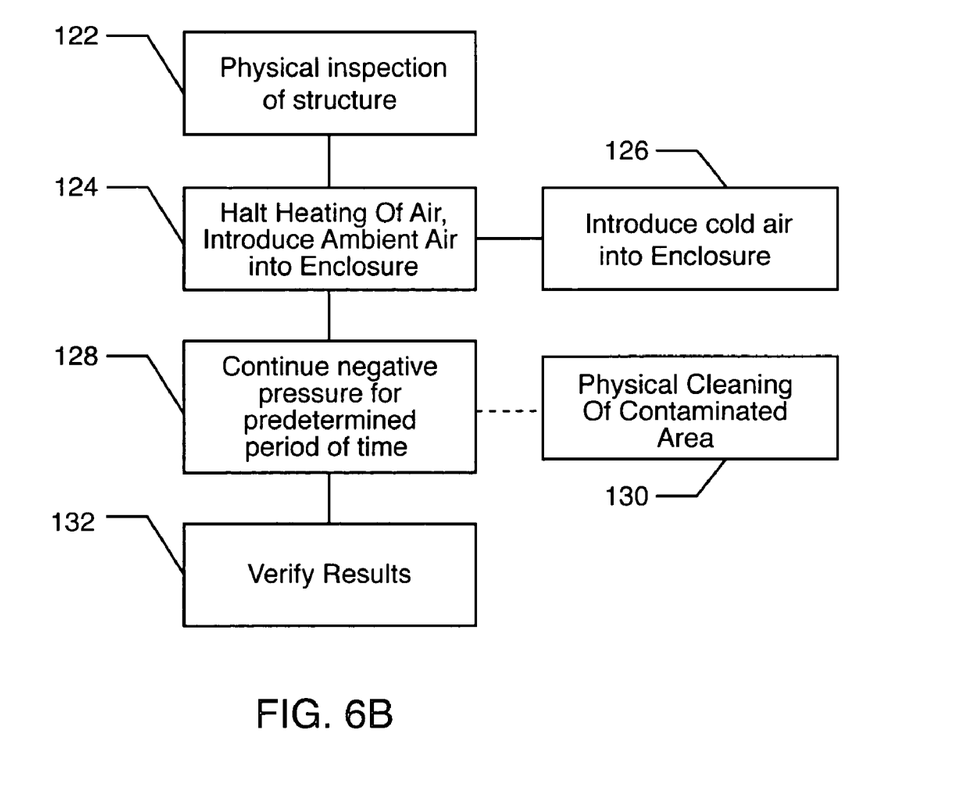

With reference now to FIG. 6B, the system of the present invention contemplates that a physical inspection of the structure (122) be conducted during the treatment process. This would involve individuals entering into the structure 12 and physically inspecting it during the treatment process. Typically, such personnel would inspect the heated area while wearing personal protection, such as respirators or "cool suits" to protect the personnel inspecting the treatment area during the heat treatment. Such inspection personnel could carry portable pressure and temperature sensing devices to confirm the operation and accuracy of the other probes. Application of biocides or physical cleaning could also be done.

After it has been determined that the harmful biological organisms and agents have been destroyed, and after sufficient drying has taken place, the heating of air is halted and non-heated ambient air is introduced into the structure (124). In one embodiment, after the structure has been heated for a predetermined period of time, the structure is then subjected to cold air (126), or the contaminated areas frozen, to further ensure that all contaminants are destroyed. Preferably, after the contaminated area or structure is frozen, any moisture remaining in the contaminated area or structure is removed, such as by the dehumidifiers 30. This may require the heating of the structure once again so that the moisture can be removed.

The negative pressure is maintained for a predetermined period of time (128). These steps are taken in order to prevent any viable fungi, molds, etc. from sporulating as such organisms when threatened with destruction will often sporulate or form cysts or the like to facilitate the survival of the organisms and their progeny. The aggressive air flow through the structure continues to remove the harmful organisms, organic substances, etc., for some time.

This entire process may often be completed in a short time, allowing a business to be closed for only one day or a residential structure to be fully treated during a typical work or school day. However, in certain circumstances, such as in the case of large structures or high levels of harmful substances within the structure, the process may be extended to several days or more to ensure that the structure is properly treated. It has been found that while harmful organisms are killed and removed during this process, the reduction of the VOCs actually continues for some time after treatment. Opening a window to allow the structure 12 to properly vent is believed to be adequate to remove these residual compounds.

In certain instances, the structure 12 is then physically cleaned (130) after the aforementioned steps have been performed. For example, when dealing with the hanta virus, the health concerns of the workers dictate that the virus be killed and removed to the greatest extent possible. Then, after the virus has been destroyed and removed to the greatest extent possible utilizing the aforementioned steps, workers can enter the structure and physically remove rodent droppings and the like which may contain the neutralized viruses. Samples and specimens may be taken of the previously contaminated areas to verify the desired results (132) and a physical examination of the structure can be used to verify the removal of the contagions and harmful substances.

Although several embodiments of the present invention have been described in detail for purposes of illustration, various modifications of each may be made without departing from the spirit and scope of the invention. Accordingly, the invention is not to be limited, except as by the appended claims.

What is claimed is:

1. A process for removing or treating a human occupiable vehicle or building structure at least partially contaminated with harmful biological and organic substances, comprising the steps of:
   substantially enclosing at least a selected area of the human occupiable structure to be treated;
   heating ambient air within the enclosed area to a temperature between 110 to 400 degrees Fahrenheit to cause harmful biological or organic substances to be destroyed or migrate into the ambient air;
   monitoring the temperature in the enclosed area until the temperature is achieved; and
   removing moisture from the air within the enclosed area.

2. The process of claim 1, including the step of providing an air inlet and an air outlet duct to the selected area.

3. The process of claim 1, depressurizing the enclosed area; monitoring the enclosed area to determine that sufficient depressurization has been established.

4. The process of claim 1, including the step of physically cleaning the contaminated area.

5. The process of claim 1, including the step of placing and distributing heated air into the enclosed area.

6. The process of claim 1, including the step of applying a biocide to the contaminated area.

7. The process of claim 1, wherein the applying step includes the step of introducing a biocide into the heated air.

8. The process of claim 6, wherein the biocide comprises a borate-based compound.

9. The process of claim 1, including the step of protecting heat-sensitive articles within the enclosed area.

10. The process of claim 1, including the step of passing the heated air from the enclosed area through an incinerator.

11. The process of claim 1, including the step of recirculating the heated air from the enclosed area either into an inlet duct or a heater attached to the inlet duct.

12. The process of claim 1, including the step of monitoring the temperature with a sensor disposed outside of the enclosed area.

13. The process of claim 1, including the step of monitoring the temperature at the air inlet or outlet duct.

14. The process of claim 1, including the step of monitoring the temperature by inserting a temperature probe into a component within the enclosure.

15. The process of claim 1, including the step of irradiating the contaminated area or air with electromagnetic waves or electron beams.

16. The process of claim 1, including the step of freezing the contaminated area after it is determined that sufficient heat treatment has occurred.

17. The process of claim 16, including the step of removing moisture from the contaminated area after the freezing step.

18. The process of claim 1, including the step of aggressively moving air within the enclosed area to aerosolize the biological and organic substances to facilitate their removal.

19. The process of claim 18, including the use of air scrubbers within the enclosed area having fans to move the air through filters for trapping particles therein.

20. The process of claim 1, including the step of directing non-heated ambient air into the enclosed area after a predetermined time of directing heated air into the enclosure.

21. The process of claim 20, including the step of passing the air through a filter, an incinerator, or an irradiation device.

22. The process of claim 1, including the step of entering the enclosed area using protective gear to inspect the contaminated areas during treatment.

23. The process of claim 22, wherein the protective gear includes protective cool suits or respirators.

24. The process of claim 1, including the step of containing the contaminated area.

25. The process of claim 1, including the step of heating building materials of a structure, vehicle or device and removing moisture therefrom prior to construction of the structure, vehicle or device.

26. A process for removing or treating a human occupiable vehicle or building structure at least partially contaminated with harmful biological and organic substances, comprising the steps of:

- substantially enclosing a selected area comprising at least a portion of the contaminated building or a vehicle;
- providing an air inlet and an air outlet duct to the enclosed area;
- containing a contaminated area within the enclosed area;
- placing and distributing heated air into the enclosed area to a temperature between 110 to 400 degrees Fahrenheit to cause harmful biological or organic substances to be destroyed or migrate into the ambient air;
- monitoring the temperature in the enclosed area until the temperature is achieved, wherein the temperature monitoring is performed by a sensor disposed outside of the enclosed area or at the air inlet or outlet duct;
- aggressively moving air within the enclosed area to aerosolize the biological and organic substances to facilitate their removal; and
- directing non-heated ambient air into the enclosed area after a predetermined time of directing heated air into the enclosure.

27. The process of claim 26, including the step of passing the air through a filter, an incinerator, or an irradiation device.

28. The process of claim 26, including the step of depressurizing the enclosed area, and monitoring the enclosed area to determine that sufficient depressurization has been established.

29. The process of claim 26, including the step of physically cleaning the contaminated area.

30. The process of claim 26, including the step of removing moisture from the air within the enclosed area.

31. The process of claim 26, including the step of applying a biocide to the contaminated area.

32. The process of claim 26, including the step of recirculating the heated air from the enclosed area into an inlet duct or a heater associated with the inlet duct.

33. The process of claim 26, including the step of irradiating the contaminated area or ambient air within the enclosure with electromagnetic waves or electron beams.

34. The process of claim 26, including the step of freezing the contaminated area after it is determined that sufficient heat treatment has occurred, and then removing moisture from the contaminated area.

35. The process of claim 26, including the step of entering the building or vehicle using protective gear including protective suits or respirators to inspect the contaminated areas during treatment.

36. A process for removing or treating a human occupiable vehicle or building structure at least partially contaminated with harmful biological and organic substances, comprising the steps of:

- substantially enclosing a selected area comprising at least a portion of the contaminated building or a vehicle;
- providing an air inlet and an air outlet duct to the enclosed area;
- placing and distributing heated air into the enclosed area to a temperature between 110 to 400 degrees Fahrenheit to cause harmful biological or organic substances to be destroyed or migrate into the ambient air;
- monitoring the temperature in the enclosed area until the temperature is achieved, wherein the temperature monitoring is performed by a sensor disposed outside of the enclosed area or at the air inlet or outlet duct;
- aggressively moving air within the enclosed area to aerosolize the biological and organic substances to facilitate their removal;
- removing moisture from the air within the enclosed area;
- passing the air through a filter, an incinerator, or an irradiation device; and
- directing non-heated ambient air into the enclosed area after a predetermined time of directing heated air into the enclosure.

37. The process of claim 36, including the step of depressurizing the enclosed area, and monitoring the enclosed area to determine that sufficient depressurization has been established.

38. The process of claim 36, including the step of physically cleaning the contaminated area.

39. The process of claim 36, including the step of applying a biocide to the contaminated area.

40. The process of claim 36, including the step of recirculating the heated air from the enclosed area into an inlet duct or a heater associated with the inlet duct.

41. The process of claim 36, including the step of irradiating the contaminated area or ambient air within the enclosure with electromagnetic waves or electron beams.

42. The process of claim 36, including the step of freezing the contaminated area after it is determined that sufficient heat treatment has occurred, and then removing moisture from the contaminated area.

43. The process of claim 36, including the step of entering the building or vehicle using protective gear including protective suits or respirators to inspect the contaminated areas during treatment.

* * * * *